US008469034B2

(12) United States Patent
Dobson et al.

(10) Patent No.: US 8,469,034 B2
(45) Date of Patent: Jun. 25, 2013

(54) STEM CELL TARGETING AND ACTIVATION USING MAGNETIC PARTICLES

(75) Inventors: Jon Dobson, Stoke-on-Trent (GB); Alicia El Haj, Highpeak (GB)

(73) Assignee: MICA Biosystems Limited, Solihull, West Midlands (GB)

(*) Notice: Subject to any disclaimer, the term of this patent is extended or adjusted under 35 U.S.C. 154(b) by 1407 days.

(21) Appl. No.: 10/596,594

(22) PCT Filed: Dec. 8, 2004

(86) PCT No.: PCT/GB2004/005156
§ 371 (c)(1),
(2), (4) Date: May 4, 2009

(87) PCT Pub. No.: WO2005/059118
PCT Pub. Date: Jun. 30, 2005

(65) Prior Publication Data
US 2011/0034753 A1 Feb. 10, 2011

(30) Foreign Application Priority Data
Dec. 18, 2003 (GB) .................................. 0329310.7

(51) Int. Cl.
*A61B 19/00* (2006.01)
(52) U.S. Cl.
USPC ....................................................... 128/898
(58) Field of Classification Search
USPC .......... 128/897–899; 600/9–15; 977/904–906
See application file for complete search history.

(56) References Cited

U.S. PATENT DOCUMENTS

| 4,105,017 | A  | 8/1978  | Ryaby et al.    |
| 5,183,336 | A  | 2/1993  | Poltorak et al. |
| 5,486,457 | A  | 1/1996  | Butler et al.   |
| 5,842,477 | A  | 12/1998 | Naughton et al. |
| 6,197,586 | B1 | 3/2001  | Bhatnagar et al.|
| 6,548,264 | B1 | 4/2003  | Tan et al.      |
| 6,649,408 | B2 | 11/2003 | Bailey et al.   |
| 2004/0147015 | A1 | 7/2004 | El-Haj et al.  |
| 2006/0093611 | A1 | 5/2006 | Haj et al.     |
| 2011/0034753 | A1 | 2/2011 | Dobson et al.  |

FOREIGN PATENT DOCUMENTS

| WO | 95/06248 A1   | 3/1995  |
| WO | 01/88540 A1   | 11/2001 |
| WO | 0232397 A2    | 4/2002  |
| WO | 02/051985 A2  | 7/2002  |
| WO | 02051985 A2   | 7/2002  |
| WO | 2004000369 A2 | 12/2003 |
| WO | 2005/059118 A3| 6/2005  |

OTHER PUBLICATIONS

Lewin, M., et al. "Tat peptide-derivatized magnetic nanoparticles allow in vivo tracking and recovery of progenitor cells," Nature Biotechnology, vol. 18, No. 4, pp. 410-414 (Apr. 2000).
Cartmell, S.H., et al. "Development of magnetic particle techniques for long-term culture of bone cells with intermittent mechanical activation," IEEE Transactions on Nanobioscience, pp. 92-97 (Jun. 2002).
Frohlich, M.W., et al. "Ex Vivo Activation and Expansion of T Cells from the Peripheral Blood of Multiple Myeloma Patients Using the Xcellerate™ Process," Blood, vol. 100, No. 11, Abstract No. 5259 (Nov. 16, 2002).
Dobson, Jon et al., "Theoretical evaluation of the magnetic force bioreactor," Internet Article, http://www.maths-in-medicine.org/uk/2001/magnetic-bioreactors (Jul. 31, 2001).
Al-Qodah, Z., "Antibiotics production in a fluidized bed reactor utilizing a transverse magnetic field," Biprocess Engineering, vol. 22, p. 299-308 (2000).
Bottlang, M. et al, "A cell strain system for small homogeneous strain application," Biomed Technik, vol. 42, pp. 305-309 (1997).
Cartmell, S.H., et al., "Preliminary analysis of magnetic particle techniques for activating mechanotransduction in bone cells," IEEE, pp. 87-88 (Jun. 6, 2002).
Dobson, Jon et al., "Application of the ferromagnetic transduction model to DC and pulsed magnetic fields: Effects on epileptogenic tissue and implications for cellular phone safety," Biochemical and biophysical research communications, vol. 227, 718-723, (1996).
Dobson, Jon et al., "Principles and design of a novel magnetic force mechanical conditioning bioreactor for tissue engineering, stem cell condition and dynamic in vitro screening," IEEE Transactions on Nanobioscience, vol. 5, No. 3 (Sep. 2006).
El Haj, A.J. et al., Magnetic nanoparticle-based tagging of mecahnosensors for bone tissue engineering (Abstract 6604), Journal of Biomechanics, vol. 39, p. S214 (2006).
El Haj, A.J. et al., "Bioreactors for bone tissue engineering," Proc. IMechE, vol. 224, Prt H., J. Engineering in Medicine, pp. 1523-1532 (Sep. 2012).
El Haj, A.J. et al., "Mechanotransduction pathways in bone: calcium fluxes and the role of voltageoperated calcium channels," Medical and Biological Engineering & Computing, vol. 37, pp. 403-409 (1999).
Glogauer, M. et al., "Magnetic fields applied to collagen-coated ferric oxide beads induce stretch-activated Ca2+ flux in fibroblasts," America Journal of Physiology, pp. C1093-C1104 (1995).
Glogauer, M. et al., "A new method for application of force to cells via ferric oxide beads," Pfugers Arch—Eur J Physiol, vol. 435, pp. 320-327(1998).
Howard, J. et al., "Compliance of the hair bundle associated with gating of mechanoelectrical transduction channels in the bullfrog's saccular hair cell," Neuron. vol. 1, pp. 189-199 (May 1988).
Hughes, Steven et al. "Expression of the mechanosensitive 2PK+ channel TREK-1 in human osteoblasts," Journal of Cellular Physiology, Vol. 206, pp. 738-748 (2006).
Hughes, Steven et al. "Magnetic targeting of mechanosensors in bone cells for tissue engineering applications," Journal of Biomechanics, vol. 40, pp. S96-S104 (2007).

(Continued)

*Primary Examiner* — John Lacyk
(74) *Attorney, Agent, or Firm* — Janet Sleath; Speckman Law Group PLLC

(57) ABSTRACT

The present invention provides a method of selectively activating and/or targeting stem cells which enables the cells to then be manipulated mechanically in a remote manner wherein the method comprises magnetically manipulating a stem cell in vivo or in vitro by the association of a magnetisable particle within the stem cell.

18 Claims, No Drawings

OTHER PUBLICATIONS

Hughes, Steven et al. "Selective activation of mechanosensitive ion channels using magnetic particles," J. R. Soc. Interface vol. 5, pp. 855-863 (2008).

Ito, Akira et al., "Medical application of functionalized magnetic nanoparticles," Journal of Bioscience and Bioengineering, vol. 100, No. 1, pp. 1-11 (2005).

Kirschvink, Joseph L., "Constraints on biological effects of weak extremely low-frequency electromagentic fields," Physical Review A, vol. 46, No. 4, pp. 2178-2187 (Aug. 15, 1992).

Kanczler, Janos M. et al., "Controlled Differentiation of Human Bone Marrow Stromal Cells Using Magnetic Nanoparticle Technology," Tissue Engineering: Part A, vol. 16, No. 10, pp. 3241-3250 (2010).

Kaspar, D. et al., "Dynamic cell stretching increases human osteoblast proliferation and CICP synthesis but decreases osteocalcin synthesis and alkaline phosphatase activity," Journal of Biomechanics, vol. 33, pp. 45-51 (2000).

Kirkham, Glen R. et al., "Hyperpolarization of Human Mesenchymal Stem Cells in Response to Magnetic Force," IEEE Transactions on Nanobioscience, vol. 9, No. 1, pp. 71-74 (Mar. 2010).

Komarova, Svetlana V. et al., "Osteclast ion channels: potential targets for antiresportive drugs," Current Pharmaceutical Design, vol. 7, pp. 637-654 (2001).

Laniado, Marc E. et al., "Voltage-Gated K+ Channel Activity in Human Prostrate Cancer Cell Lines of Markedly Different Metastatic Potential: Distinguishing Characteristics of PC-3 and LNCaP Cells," The Prostrate, vol. 46, pp. 262-274 (2001).

Liu, Mingyao et al., "Bio-stretch, a computerized cell strain apparatus for three-dimensional organotypic cultures," In Vitro Cell. Dev. Biol. Animal, vol. 35, pp. 87-93 (Feb. 1999).

Maingret, Francois et al., "Mechano- or Acid Stimulation, Two Interactive Modes of Activation of the TREK-1 Potassium Channel," The Journal of Biological Chemistry, vol. 274, No. 38, pp. 26691-26696 (Sep. 17, 1999).

Shoda, Makato "Effect of Magnetic Fields on Living Cells," Abstract, Journal of the Brewing Society of Japan, vol. 89, No. 9, pp. 710-716 (1994).

Mykhaylyk, O.M. et al., "Signal transduction of erythrocytes after specific binding of ecdysterone and cholesterol immobilized on nanodispersed magnetite," Journal of Magnetism and Magnetic Materials, vol. 225, pp. 226-234 (2001).

Wang, Ning "Mechanical interactions among cytoskeletal filaments," Hypertension, vol. 32, pp. 162-165 (Jul. 2008).

O'Grady, Scott M. et al., "Molecular diversity and function of voltage-gated (Kv) potassium channels in epithelial cells, "The International Journal of Biochemistry and Cell Biology, vol. 37, pp. 1578-1594 (2005).

Pardoe, Heath et al., "Structural and magnetic properties of nanoscale iron oxide particles synthesized in the prsence of dextran or polyvinyl alcohol," Journal of Magnetism and Magentic Materials vol. 225, pp. 41-46 (2001).

Pound, Jodie C. et al., "Strategies to Promote Chondrogenesis and Osteogenesis from Human Bone Marrow Cells and Articular Chondrocytes Encapsulated in Polysaccharide Templates," Tissue Engineering, vol. 12, No. 10, pp. 2789-2780 (2006).

Santra, Swadeshmukul et al., "Synthesis and characterization of silica-coated iron oxide nanoparticles in microemulsion: the effect of nonionic surfactants," Langmuir, vol. 17, pp. 2900-2906 (2001).

Schmidt, Christian et al., "Mechanical stressing of integrin receptors induces enhanced tyrosine phosphorylation of cytoskeletally anchored proteins," The Journal of Biological Chemistry, vol. 273, No. 9, pp. 5081-5085 (Feb. 27, 1998).

Schutt, W. et al., "Applications of magnetic targeting in diagnosis and therapy-possibilites and limitations: a mini-review," Hybridoma vol. 16, No. 1, pp. 109-117 (1997).

Smalt, R. et al., Induction of NO and prostaglandin E2 in osteolasts by wall-shear stress but not mechanical strain. Am. J. Physiol. Endocrinol. Metab., vol. 273, pp. E751-E758 (1997).

Ullrich, N. et al., "Expression of voltage-activated chloride currents in acute slices of human gliomas," Neuroscience, vol. 83, No. 4, pp. 1161-1173 (1998).

Walker, L.M. et al., "Calcium-channel activation and matrix protein upregulation in bone cells in response to mechanical strain," Journal of Cellular Biology, vol. 79, pp. 648-661 (2000).

Wang, Ning et al., "Control of cytoskeletal mechanics by extracellular matrix, cell shape, and mechanical tension," Biophysical Journal, vol. 66, pp. 2181-2189 (Jun. 1994).

Wang, Ning et al., "Contribution of intermediate filaments to cell stiffness, stiffening, and growth," Am. J. Physiol. Cell Physiol., vol. 279, pp. C188-C194 (2000).

Wang, J. et al., "Force regulates smooth muscle actin in cardiac fibroblasts," Am. J. Physiol. Heart Circ. Physiol., vol. 279, pp. H2776-H2785 (2000).

Wolbank, S. et al., "In vivo tracking of stem cells using magnetic tagging in a nude mouse model (Abstract 7855)," Journal of Biomechanics, vol. 39, p. S447 (2006).

Yanese, Mitsugu et al., "Intracellular hyperthermia for cancer using magnetite cationic liposomes: an in vivo study," Japanese Journal of Cancer Research, vol. 89, pp. 463-470 (Apr. 1998).

Yanese, Mitsugu et al., Intracellular hyperthermia for cancer using magnetite cationic liposomes: An ex vivo study, Japanese Journal of Cancer Research, vol. 88 pp. 630-632 (Jul. 1997).

Yang, Ying et al., "Development of a mechano-active scaffold for tissue engineering," Biomaterials, vol. 23, pp. 2119-2126 (2002).

Yuge, Louis et al., "Differentiation of myoblasts is accelerated in culture in a magnetic field," In Vitro Cell Dev. Biol. Animal, vol. 36, pp. 383-386 (Jun. 2000).

STEM CELL TARGETING AND ACTIVATION USING MAGNETIC PARTICLES

REFERENCE TO RELATED APPLICATIONS

This application is the US national phase entry of International Patent Application no. PCT/GB04/05156, filed Dec. 8, 2004, which claims priority to UK Patent Application no. 0329310.7, filed Dec. 18, 2003.

FIELD OF THE INVENTION

This invention relates to a novel method of magnetically manipulating stem cells ex vivo or in vivo and to methods of treatment related thereto.

BACKGROUND

The use of stem cells in the form of a cell-based therapies is currently one of the most exciting and promising areas for disease treatment and reparative medicine. Clearly, basic research into the ways by which proliferation and differentiation of e.g. embryonic and adult stem cells can be controlled is vitally important.

U.S. Pat. No. 6,548,264 describes silica coated nanoparticles which comprise a magnetic metal core. The magnetic core present in the particles enables the particles to be responsive to a magnetic field and therefore, the particles are suitable for use in diagnostic, imaging and recording systems. However, the nanoparticles of the prior art may suffer from the disadvantage that they do not define the method of activation at a cellular level.

Magnetic bead twisting cytometry has been used to define the mechanical properties of single cells and to demonstrate that external mechanical forces can be transmitted across the cell surface and through the cytoskeleton via transmembrane cell adhesion molecules such as integrins, see, for example, Wang, N and Ingberger, D E (1995) Probing transmembrane mechanical coupling and cytomechanics using magnetic twisting cytometry. *Biochem. Cell Biol.* 73: 327-335.

There have been many developments in biocompatible magnet nanoparticle synthesis, characterization[1-3] and applications of novel magnetic techniques in the field of healthcare[4-6]. This work primarily has involved investigating the controlled and directed transport of pharmaceuticals. In these systems therapeutic drugs or genes may be attached to magnetic carrier particles (usually polymer coated magnetite), which are then concentrated at the target site in vivo by the application of spatially focused, high gradient magnetic fields. Once the drug/carrier complexes have accumulated at the target site, the drug is released and uptake at the sites is enhanced. Investigations have been made into new methods for magnetic targeting for gene therapy as well as theoretically and experimentally examining and improving deposition of magnetic micro- and nanoparticle carriers in model systems in vitro and in vivo[4,6].

Short-term experiments where force is applied to the cell membrane using torque or where tension is applied to transmembrane proteins such as RGD or collagen molecules has been described by a number of researchers[7,8]. These experiments use 'mechanical' stimulation of the membrane to trigger short term internal calcium fluxes in a variety of cells. It is known that mechanical signalling using other techniques can trigger differentiation pathways in bone marrow stromal cells down the osteogenic lineage[11] and in particular, that low level mechanical signals across the membrane can up-regulate expression and DNA binding activity of osteoblastic specific transcription factors, cbfa1 and cfos[12,13].

In these investigations, force can be applied to a number of different tagged receptors. It has been demonstrated how we can influence downstream processes and enhance collagen and other matrix protein synthesis[15]. Using bone marrow derived mesenchymal stem cells conditioned to differentiate along the osteogenic and chondrogenic lineage we have been investigating downstream gene regulation in response to magnetic particle activation of specific receptors. Preliminary data has shown an up-regulation in Runx 2 in response to magnetic particle stimulation of calcium channels in human mesenchymal stem cells followed by up-regulation of a mechanosensitive matrix protein, osteopontin. In addition, we have evidence of up-regulation of SOX 9 following stimulation of monolayer human dedifferentiated chondrocytes. These studies have been extended to 3D analysis of cell-seeded scaffolds over long-term culture to investigate the use of these strategies for construct fabrication in tissue engineering in vitro. Furthermore, preliminary studies which include a dose-response analysis of particle number and force applied are encouraging and indicate increased matrix synthesis and expression of the osteogenic phenotype[14].

Bone marrow contains multipotential stromal stem cells or mesenchymal stem cells which can differentiate into, inter alia, fibroblastic, osteogenic, adipogenic and reticular cells. These mesenchymal stem cells, such as human bone marrow stromal fibroblasts can be isolated from volunteer donors and may retain their multilineage (adipocytic, chondrogenic, osteoblastic) potential. One advantage in the use and manipulation of the aforementioned cells lies in their lack of immunogenicity which provides the potential for use of these cells in, inter alia, cartilage and bone repair.

Our as yet unpublished co-pending International Patent Application, No. PCT/GB2003/002624 combines the magnetic nanoparticle approach with knowledge of mechanosensitive ion channels, in particular, the TREK K+ channel. It is established that the TREK channel is present in osteogenic, chondrogenic and bone marrow stromal cells In order to define more closely the targeting of specific receptors to control activation, we have used HIS-tagged clones of the TREK gene. HIS tags have been inserted into particular regions of the TREK molecule to allow attachment of HIS antibody or $NI^{2+}$ bound magnetic particles which can then be remotely torques using a magnetic field. Sites of the ion channel protein which lie both internal and external to the cell membrane have been tagged and in this way we can identify the mechanosensitive regions of the molecule as well as define the signal frequencies required to switch on downstream processes. FIG. 2 shows the results of experiments using bone marrow stromal cells with internal calcium levels up-regulated as a result of the application of magnetic fields to magnetic nanoparticles attached to a His-tagged TREK channel.

It has been shown that conditioning connective tissue cells in vitro can be achieved, by, inter alia, the development of a magnetic force bioreactor which enables magnetic fields to be applied in vitro to 2D monolayer cultures and 3D cell-seeded scaffolds.

However, neither US '264 nor Wang solve or even address the problems surrounding two fundamental questions which need to be addressed, and which encompass the ultimate goal of engineering cells for clinical use, namely;
(i) how will cells be targeted to the site of repair and held at that site; and
(ii) how will cells e.g. stem cells, be conditioned or differentiated in vitro and/or in vivo.

SUMMARY

We have now surprisingly found ways by which stem cells tagged with magnetic nanoparticles can be delivered to or held at, a particular repair site by external magnetic manipulation. In addition, we have developed these concepts further to include remote activation of specific cellular membrane receptors, which in essence, involves localising cells e.g. stem cells. More simply this involves deposition of stem cells at a site e.g. a repair site, retaining the cells at the site and remotely activating the cells in situ within the patient.

In particular, the present invention addresses issues of targeting specific receptors on cells for remote activation of transmembrane ion channels in stem cells. Importantly, magnetic nanoparticle-based technologies are increasingly used clinically, in many facets of healthcare e.g. contrast enhancement for MRI.

In the present invention we have achieved early stages of differentiation of these cell types. Moreover, the achieved differentiation acts as a model for binding strategies which allows both remote targeting within the body and/or activation at specific sites when localised.

Thus, the present invention enables the targeting of a variety of stem cell receptor types, such as mechano-activated ion channels e.g. K+ channels (TREK), calcium channels, integrins and surface membrane binding sites such as RGD, present in human bone marrow stem cells. Importantly, such receptors have the potential for remote activation. The targeting of other known receptors, such as external growth factors (e.g. TGFB and BMP2) which have been shown to activate downstream transcription factors such as Runx2 and Osterix, critical for stem cell differentiation can also be achieved.

Thus, the present invention provides the opportunity for true engraftment of, inter alia, human mesenchymal stem cells, long-term biological effects on the stem cells at the site of injury or repair. Furthermore, the ability to select, expand and differentiate these cells and target the cells using magnetic nanoparticles is especially advantageous. Furthermore, utilisation of the present invention provides therapeutic implications in, inter alia, gene therapy and tissue engineering.

Biocompatible magnetic nanoparticles, primarily composed of a magnetite ($Fe_3O_4$) and/or maghemite ($Fe_2O_3$) core with either a silica, dextran, or PVA coating may be utilised in the present invention. Such particles may be synthesized following methods known in the art. However, it will be understood that other magnetic nanoparticles may be utilised. Particle sizes can range from ~10 nm up to a few microns e.g. 1 to 10 μm. Commercially available magnetic micro- and nanoparticles with varying surface chemistry may also be used. The coatings may be functionalized and crosslinked to membrane attachment motifs such as those described above. The magnetic nanoparticles may be modified so as to customise, inter alia, particle internalization frequency and binding efficiency and stability will be examined as will the effects of binding on cell viability and function. Modification may also include customisation of internal binding sites as well as sites on the outer membrane. A variety of coatings may be used in magnetic nanoparticle binding and loading in human osteoblasts[14,15] and these techniques may be further optimized for stem cell binding, delivery and activation e.g. using adult primary marrow human stem cells and/or human embryonic stem cells.

Targeting

Conventionally known high gradient magnets, e.g. external rare earth (primarily NdFeB), high-gradient magnets, may be used to target the stem cells to specific sites within an in vitro test system and/or in vivo. Clearly, it is a preferred aspect of the invention to target the stem cells in vivo. Such magnets produce high field/gradient products which exert a translational force on the magnetic particles loaded onto the cells, holding them at the target site according to the equation:

$$F_{mag} = (X_2 - X_1)V\frac{1}{\mu_o}B(\nabla B)$$

Activation

Remote mechanical activation may be achieved using e.g. a magnetic conditioning bioreactor. Such bioreactors, which are known per se, enable forces to be applied to magnetic particles attached to cells cultured in vitro within a multi-well 2D system or in vivo a 3D scaffold-based system. Stem cells, e.g. Mesenchymal stem cells and populations generated therefrom, such as osteogenic, chondrogenic and adipogenic populations may be isolated using, for example, magnetic activated cell sorting (MACS) with a monoclonal antibody e.g. STRO-1 using standard protocols known per se[14]. Such protocols include those known for BMSc culture in monolayer and using 3D scaffolds composed of biodegradable polymers such as poly lactic acid (PLLA) or collagen gels[21].

We have now found a method of selectively activating and/or targeting stem cells which enables the cells to then be manipulated mechanically in a remote manner.

By the term "in a remote manner" it is intended to mean, e.g. a non-contacting manner and in the case of in vivo activating/targeting specifically from outside the body.

Thus according to the invention we provide a method of magnetically manipulating a stem cell in vivo or in vitro which comprises the association of a magnetisable particle with a stem cell.

The method may comprise ex vivo manipulation of an in vivo process. Furthermore, it will be understood by the skilled man that a reference to a cell shall be construed to include a plurality of cells.

More particularly, the invention provides a method as hereinbefore described which comprises the activation and/or targeting of a magnetisable particle with a stem cell as hereinbefore described.

According to a further aspect of the invention we provide a method of magnetically manipulating a stem cell which comprises the association of a magnetisable particle with a cell characterised in that the method comprises agonising or antagonising ion channels within a cell by the association of a magnetisable particle with a cell.

According to a yet further aspect of the invention we provide a method as hereinbefore described which include a differentiation step.

In this aspect of the invention the magnetisable particle may be associated directly with the cell. Alternatively, the method may comprise associating the magnetisable particle with an antibody, enzyme, etc., which is subsequently associated with the cell.

The association of a magnetisable particle with a cell may comprise the introduction of such a particle into a cell, the attachment of such a particle to a cell, e.g. externally or internally to a cell, or any combination thereof. Thus, the magnetisable particles may be associated intracellularly or extracellularly or a combination of intracellularly and extracellularly. However, in a preferred aspect of the invention the particles are associated intracellularly.

When the method of the invention comprises intracellular association this will comprise association with an internal binding site. By way of example only, for TREK-1, the particle(s) may be associated with the N-terminus region of the ion channel. Alternatively, the particle(s) may be associated with the COOH terminus region of the ion channel. It will be appreciated by one skilled in the art that numerous ion channels and binding sites may be utilised in the method of the invention. Thus, internal binding sites which correspond to the N-terminus region of the ion channel, as seen in TREK-1 or which corresponds to the COOH terminus region of the ion channel. as seen in TREK-1 may be utilised as well as other binding sites known per se.

Thus, we also provide a method of manipulating a mechanosensitive ion channel characterised in that the method comprises the association of a magnetisable particle with an ion channel, either directly or indirectly.

The method of the invention may comprise the manipulation of mammalian cells or other cell types, such as bacterial cells, plant cells, etc. However, it will be understood by the skilled man that the method of the present invention may be used to manipulate other cell types not mentioned herein. Furthermore, the method may be an in vitro method or an in vivo method, although an in vivo method is preferred.

The method of the invention may comprise the up-regulation or down-regulation of gene expression in stem cells in response to mechanical manipulation of the stem cells as described herein. Through the manipulation of gene expression patterns or levels, the stem cells may be induced to follow particular differentiation pathways such as described herein.

Preferentially, the method of the invention comprises the remote manipulation of cells and/or of agonising or autagonising ion channels, e.g. manipulation from outside the body, i.e. remote mechanical activation.

The method of the invention may be utilised in relation to a variety of cells which are known per se. However, preferentially, the method is suitable for use with mammalian stem cells.

The method of the invention may be utilised in connection with any conventionally known ion channels within the cell which are hereinbefore described. The method is especially suited for use in mechanosensitive ion channels. Such mechanosensitive ion channels have been identified in many cell types and have been predominantly described as calcium or potassium ion channels, although it should be understood that the method of the invention is not limited to use in relation to calcium or potassium ion channels. By way of example only, one such channel which has been well characterised at the molecular level and at the functional level in neuronal cells is the chromosomal gene TREK-1, which is part of the 2P K+ channel family. TREK-1 channels, have been identified in bone cells, and are known to respond to shear stress, cell swelling and membrane stretch as well as other external agents such as fatty acids and general anaesthetics.

A particular aspect of the present invention is to provide a method of manipulating mechanosensitive ion channels.

These "mechanosensitive" ion channels are present in a variety of mammalian, e.g. human, and bacterial cells and the present invention enables the cells to be selectively activated in the body and/or in cell cultures, see, for example, Sokabe, M, F Sachs, A Jing (1991) Quantitative video microscopy of patch clamped membranes: Stress, strain, capacitance, and stretch channel activation. *Biophys J.* 59: 722-728; Stewart, Z, B Martinac and J Dobson (2000) Evidence for mechanosensitive transmembrane ion channels of small conductance in magnetotactic bacteria. *Electro- and Magnetobiol.* 19: 81-89. As these channels are instrumental in normal cellular function and play a particularly important role in, for example, the production of bone and connective tissue or activation of the peripheral nervous system, the ability to manipulate them remotely, e.g. from outside the body, is especially advantageous an provides applications in, inter alia, pain relief, e.g. anaesthetics, therapeutics, tissue engineering and repair and cancer therapy.

In a further aspect of the invention the method may also be suitable for use with conventionally non mechanosensitive cells and/or ion channels by the transfection of channels into cells which may otherwise be otherwise non-responsive.

All ion channels open and close (i.e. change conformational state) in response to forces and this is the principle behind ion channel activation. In the case of mechanosensitive ion channels, the force results in membrane deformation, triggering the opening of the channel. Voltage-gated and ligand-gated ion channels are also "mechanoresponsive" in that they respond to mechanical stresses on the ion channel generated by coulomb forces (in the case of voltage-gated channels) and binding forces (in the case of ligand-gated channels). As such, all ion channels can be activated by the method described herein provided that the magnetisable particle is coupled, either directly or indirectly, to the mechano-responsive region of the channel protein.

Thus, in one aspect of the present invention the ion channel is a voltage-gated ion channel, alternatively, the ion channel is a ligand-gated ion channel.

A wide variety of particles may be used in the method of the invention. The magnetisable particle used in the method of the invention may be inherently magnetic or, alternatively, may be one which reacts in a magnetic field. Generally, any magnetic material may be used, however, by the term magnetic we mean, for example, a material which is paramagnetic superparamagnetic, ferromagnetic and/or antiferromagnetic, examples of which include elemental iron (Fe), or an compound, e.g. an iron salt, such as, magnetite ($Fe_3O_4$), maghemite ($\gamma Fe_2O_3$), and greigite ($Fe_3S_4$), or a chromium compound, e.g. a chromium salt, such as chromium oxide ($CrO_2$), or any combination thereof. Preferably the magnetic material comprises particles, e.g. nanoparticles, which comprises a magnetic core with a biocompatible coating. Thus, such preferred particles are nanoparticles and especially nanoparticles having a core and, e.g. a silica shell enveloping the core. However, also porous particles with multiple magnetic centres within the pores. An example of such particles are those nanoparticles described in U.S. Pat. No. 6,548,264 which is incorporated herein by reference. Thus, the prior art nanoparticles may have a mean size of less than 1 micron, each of said nanoparticles comprising (a) a core comprising a magnetisable particle and (b) a silica shell enveloping the core, wherein the magnetisable particle is a magnetic material as hereinbefore described.

The micro- and nano-particles (intended to be attached to the cells) will generally be substantially spherical or elliptical. The size of the particles may vary according, inter alia, to the nature of the magnetisable material, the application, etc. However, an example of particles may be nanoparticles can having a mean size, e.g. diameter, of 5000 nm or less, e.g. from 1 nm to 5000 nm, preferably from 1 nm to 1000 nm, more preferably from 1 nm to 300 nm, or from 2 nm to 10 nm).

The particles for attachment to the cells may be coated or uncoated and single or multi-domain. Examples of suitable particles include, but are not limited to:
(i) Coated magnetic microspheres (d=4 μm) available from Spherotech, Inc. These microspheres consist of a magnetically blocked core-coated by a polymer.
(ii) Single-domain, ferrite-doped silica nanoparticles with tunable size (d=50-300 nm) and narrow size distribution.

In the method of the invention the ion channels may be activated by attaching the magnetisable particles as hereinbefore described to specific regions of the cellular membrane and/or to specific "receptors" on the ion channels themselves. Thus, the mechanical forces required to activate the channels can then be applied remotely by a magnetic field acting on these magnetic particles.

In particular the method of the invention comprises modifying a magnetisable particle as hereinbefore described by tagging the particle with one or more specific antibodies or protein binding motifs which recognise key cellular elements within a cell. These include transmembrane adhesion molecules, such as integrins, cadherins, selectins, and immunoglobulins or dispersed membrane adhesion proteins such as RGD (arginine-glycine-aspartate), see, for example, J. Chen, B. Fabry, E. L. Schiffrin, and N. Wang (2001) Twisting integrin receptors increases endothelin-1 gene expression in endothelial cells *Am J Physiol Cell Physiol.* 280: 1475-84; A. R. Bausch, U. Hellerer, M. Essler, M. Aepfelbacher, and E. Sackmann (2001) Rapid stiffening of integrin receptor-actin linkages in endothelial cells stimulated with thrombin: a magnetic bead microrheology study *Biophys J* 80: 2649-57; Cartmell, S H, J Dobson, S Verschueren, A El Haj (2002) Development of magnetic particle techniques for long-term culture of bone cells with intermittent mechanical activation. *IEEE Transactions on NanoBioscience* 1: 92-97.

The method of the invention is especially advantageous because it provides a method of treatment of a variety of disorders. Indeed the invention provides a method of treatment which is applicable to any disorder in which one or more ion channels play a role. In addition, the invention provides a method for potential control of ion channel activation including pain relief, e.g. an anaesthetic role.

Thus according to the invention we provide a method of treatment of a patient suffering from a disorder in which an ion channel plays a role which comprises the administration to such a patient of magnetisable nanoparticles as hereinbefore described and manipulating those particles using a magnetic field.

The method of treatment as hereinbefore described should not be considered to be limited, but it is especially advantageous in tissue and/or bone repair. The method of treatment can be to facilitate further treatment by providing a method of pain relief, e.g. for localised anaesthesia, to targeted regions of the body.

The nature of such cells may vary depending upon the nature of the tissue of interest. For example, the cells may be ligamentum cells for growing new ligaments, tenocytes for growing new tendon. Alternatively, the cells may be chondrocytes and/or other stromal cells, such as chondrocyte progenitor cells.

Thus the method of the invention may include the regeneration of tissue or the generation of artificial tissue, such as skin, cartilage, ligament, tendon, muscle or bone.

Alternatively the method may comprise wound healing and/or tissue adhesion.

In a preferred embodiment the method may comprise bone repair and/or bone growth.

In a yet further alternative the method of the invention may include, for example, dental applications and/or veterinary applications.

The method also may be used as a mechanism for selectively killing cells (such as tumour cells) in vivo. In this case, magnetisable particles are attached to the target cell membrane or ion channel protein and a magnetic field is applied to the in vivo target region. The rapid, cyclic opening and closing (via the application of a time varying magnetic field), and/or the holding open (via the application of a static magnetic field) of ion channels in the cell membrane allows ions (such as $Ca^{++}$) to flood the cell, inducing osmotic shock and, consequently, cell death.

Thus, according to this aspect of the invention we also provide a method of destroying cells or inhibiting cell growth which comprises agonising or antagonising ion channels within a cell which by the association of a magnetisable particle with a cell.

The method may comprise a method of inducing osmotic shock to a cell, e.g. by agonising or antagonising ion channels within a cell by the association of a magnetisable particle with a cell. The method is especially useful in the treatment or alleviation of a tumour cell, e.g. a cancer cell.

Thus, the method may comprise the killing of cells by holding ion channels open with a targeted static magnetic field. Alternatively, the method may comprise the killing of cells via cyclically opening and closing ion channels with a targeted, time-varying magnetic field.

In the methods of the invention the magnetic field may be varied depending upon, inter alia, the nature of the disorder to be treated, but may be, for example, at a frequency of from 0.1 to 10 Hz. But, frequencies outside this range can also be used. The magnetic field will typically have a flux density in the order of (but not limited to) 10 mT to 1400 mT.

In the method of the invention the magnetic field may be generated outside the body for the case of in vivo applications, and may be provided by a permanent magnet or an electromagnet. The magnetic field may be a constant or a variable field, e.g. a permanent magnet may be moved relative to the cells. In the case of an electromagnet, a magnetic field may be generated by provision of appropriate electric current levels to the electromagnetic, optionally, in combination with alternating current.

According to a yet further aspect of the invention we provide a method of inducing a therapeutic effect in a cell which comprises agonising or antagonising ion channels within the cell by the association of a magnetisable particle with the cell and magnetically manipulating the magnetisable particle.

In addition we provide a method of treatment which comprises the administration of a therapeutically active agent which may be administered simultaneously, separately or sequentially with a magnetisable particle whilst agonising or antagonising ion channels within the cell.

We also provide a method of targeting a therapeutically active agent to a cell which comprises agonising or antagonising ion channels within the cell by the association of a magnetisable particle with the cell, magnetically manipulating the magnetisable particle and simultaneously, separately or sequentially administering the therapeutically active agent.

According to a yet further aspect of the invention we also provide the use of a magnetisable particle in a method of magnetically manipulating cells in vivo The use may comprise ex vivo manipulation of an in vivo process. More particularly, the invention provides the use of a magnetisable particle in the manufacture of a system for magnetically manipulating a cell which system comprises the association of a magnetisable particle with a cell and agonising or antagonising ion channels within the cell.

In this aspect of the invention the magnetisable particle may be associated directly with the cell. Alternatively, the use may comprise associating the magnetisable particle with an antibody, enzyme, etc., which is subsequently associated with the cell.

When the use of the invention comprises intracellular association. By way of example only, for TREK-1, the particle(s) may be associated with the N-terminus region of the ion channel. Alternatively, the particle(s) may be associated with the COOH terminus region of the ion channel.

The use of the invention may comprise the manipulation of mammalian cells or other cell types, such as bacterial cells, plant cells, etc. The use may be an in vitro use or an in vivo use, although an in vivo use is preferred.

Preferentially, the use of the invention comprises the remote manipulation of cells and/or of agonising or autagonising ion channels, e.g. manipulation from outside the body, i.e. remote mechanical activation.

The use of the invention may be utilised in relation to a variety of cells, which are known per se. However, preferentially, the use is suitable for use with mammalian somatic cells, for example, bone, cartilage, muscle (skeletal and cardiac) lymphatic cells, endocrine cells, urinary system cells, cells relating to the reproduction system, neuronal cells and tumour cells.

The use of the invention may be utilised in connection with any conventionally known ion channels within the cell, which is hereinbefore described. The use is especially suited for use in mechanosensitive ion channels hereinbefore described.

A particular aspect of the present invention is to provide the use in the manufacture of a system for manipulating mechanosensitive ion channels.

In a further aspect of the invention the use may also be suitable for use with conventionally non mechanosensitive cells and/or ion channels by the transfection of channels' into cells which may otherwise be otherwise non-responsive.

In one aspect of the present invention the ion channel is a voltage-gated ion channel, alternatively, the ion channel is a ligand-gated ion channel.

A wide variety of particles may be used in the use of the invention. Generally, any magnetisable material may be used, examples of which include elemental iron (Fe), or an iron compound, e.g. an iron salt, such as, magnetite ($Fe_3O_4$), maghemite ($\gamma Fe_2O_3$), and greigite ($Fe_3S_4$), or a chromium compound, e.g. a chromium salt, such as, chromium oxide ($CrO_2$), or any combination thereof. Preferably the magnetic material comprises particles which comprises a magnetic core with a biocompatible coating. Thus, such preferred particles are nanoparticles and especially nanoparticles having a core and, e.g. a silica shell enveloping the core. However, also porous particles with multiple magnetic centres within the pores. An example of such particles are those nanoparticles described in U.S. Pat. No. 6,548,264 which is incorporated herein by reference.

In particular the use of the invention comprises modifying a magnetisable particle as hereinbefore described by tagging the particle with one or more specific antibodies or protein binding motifs which recognise key cellular elements within a cell. These include transmembrane adhesion molecules, such as integrins, cadherins, selectins, and immunoglobulins or dispersed membrane adhesion proteins such as RGD (arginine-glycine-aspartate).

The use of the invention is especially advantageous because it provides a system suitable for use in the treatment of a variety of disorders. Indeed the invention provides the use in the manufacture of a medicament suitable for a treatment, which is applicable to any disorder in which one or more ion channels play a role. In addition, the invention provides the use for potential control of ion channel activation including pain relief, e.g. an anaesthetic role.

Thus, according to the invention we provide the use of a magnetisable particle in the manufacture of a medicament suitable for the treatment of a patient suffering from a disorder in which an ion channel plays a role which comprises the administration to such a patient of magnetisable particles as hereinbefore described and manipulating those particles using a magnetic field.

The use as hereinbefore described should not be considered to be limited, but it is especially advantageous in tissue and/or bone repair. The use can be to facilitate further treatment by providing a method of pain relief, e.g. for localised anaesthesia, to targeted regions of the body.

The nature of such cells may vary depending upon the nature of the tissue of interest. For example, the cells may be ligamentum cells for growing new ligaments, tenocytes for growing new tendon. Alternatively, the cells may be chondrocytes and/or other stromal cells, such as chondrocyte progenitor cells.

Thus, the use may include the regeneration of tissue or the generation of artificial tissue, such as skin, cartilage, ligament, tendon, muscle or bone.

Alternatively the use may comprise wound healing and/or tissue adhesion.

In a preferred embodiment the use may comprise bone repair and/or bone growth.

In a yet further alternative the use of the invention may include, for example, dental applications and/or veterinary applications.

The use also may be used as a mechanism for selectively killing cells (such as tumour cells) in vivo as hereinbefore described.

Thus, according to this aspect of the invention we also provide the use of a magnetisable particle in the manufacture of a system for destroying cells or inhibiting cell growth which comprises agonising or antagonising ion channels within a cell which by the association of a magnetisable particle with a cell.

The use may comprise use in a method of inducing osmotic shock to a cell, e.g. by agonising or antagonising ion channels within a cell by the association of a magnetisable particle with a cell. The use in this aspect of the invention is especially useful in the treatment or alleviation of a tumour cell, e.g. a cancer cell.

Thus, the use may comprise the killing of cells by holding ion channels open with a targeted static magnetic field. Alternatively, the use may comprise the killing of cells via cyclically opening and closing ion channels with a targeted, time-varying magnetic field.

According to a yet further aspect of the invention we provide the use of a magnetisable particle in the manufacture of a system for inducing a therapeutic effect in a cell which comprises agonising or antagonising ion channels within the cell by the association of a magnetisable particle with the cell and magnetically manipulating the magnetisable particle.

In addition we provide the use of a magnetisable particle in the manufacture of a system comprising a therapeutically active agent which may be administered simultaneously, separately or sequentially with the magnetisable particle whilst agonising or antagonising ion channels within the cell.

We also provide the use of a magnetisable particle in the manufacture of a system for targeting a therapeutically active agent to a cell which comprises agonising or antagonising ion channels within the cell by the association of a magnetisable particle with the cell, magnetically manipulating the magnetisable particle and simultaneously, separately or sequentially administering the therapeutically active agent.

According to a yet further aspect of the invention we provide a kit comprising a therapeutically active agent and means for associating a magnetisable particle with a cell.

It will be understood by the skilled that any conventionally known therapeutically active agent or a combination of therapeutically active agents may be utilised in the kit of the invention.

Thus, the kit may comprise a vessel containing a therapeutically active agent, a source of magnetisable particles and instructions for the simultaneous, sequential or separate administration thereof. The kit of the invention may also include other agents known per se. The invention may also include the use of a kit as hereinbefore described in the manufacture of a medicament.

BRIEF DESCRIPTION OF THE DRAWINGS

The invention will now be described by way of example only and with reference to the accompanying drawings in which FIG. 1a) is a schematic representation of the structure of TREK-1 showing the three sites of 12× histidine insertions for tagging magnetic beads for mechanical manipulation;

FIG. 1b) illustrates primary human astrocytes with membrane bound RGD coated carboxyl ferromagnetic particles (4 µm) (magnification×1000);

FIG. 2 is a schematic of the TREK ion channel showing structure and location of the His. tags present in the protein. Red circles indicate the sites of the His tags at the three sites, the primary loop, the COOH terminus and the NH terminus;

FIG. 3 is a representation of the magnetic activation of Trek-1 monitored via downstream changes in intracellular calcium; and FIG. 4 is a representation of the magnetic activation of TREK-1 induces transient rise in intracellular calcium in HEK293 T cells co-transfected with and Flashpericam.

DETAILED DESCRIPTION

EXAMPLE 1

Targeting Model System

The model system consists of a peristaltic pump connected to tubing which feeds into channels within agar gel blocks. The magnets can be placed at various positions in relation to the channels and the magnetic field and gradient at the target site is measured using an axial Hall probe interfaced to a gaussmeter. The magnetic fields generated by the rare earth magnets will be characterised using a Redcliffe Diagnostics MagScan field mapping system requested for this project. After each experimental run, the gel channel will be excised and assayed for cell capture using staining techniques. Magnetic particle capture will be quantified by performing Superconducting Quantum Interference Device (SQUID) magnetometry measurements on the freeze dried gel blocks. Models may be used to optimize the delivery and targeting parameters, such as magnetic field strength and geometry, magnetic particle characteristics, number of particles per cell, etc.

EXAMPLE 2

Non-specific Membrane Deformation Using Magnetic Cytometry

Specifically, scaffolds are seeded with $10^6$-$10^9$ BMSc dependant on scaffold size and cultured for 24 hours prior to placing within the bioreactor. Constructs are then subjected to varying magnetic loading regimes, e.g. 1 hour at 1 Hz frequency with forces ranging from 1-100 pN per particle. These parameters are controllable and will allow optimisation of the system for varying cell types and scaffold materials. Following treatment, cells may be removed and subjected to RNA and protein analysis at varying points after activation. Using Western blotting, FACs analysis and quantitative PCR techniques assays may be conducted for osteoblastic transcription factors, such as runx 2 and osterix, alongside matrix proteins, such as osteopontin, collagen type 1, alkaline phosphatase and osteocalcin.

EXAMPLE 3

Demonstration of New Bone Formation in Animal Models to Validate the Applicability of these Magnetic Micro and Nanoparticles Animal trials of this technology support the ability to remotely activate stem cells to promote bone call differentiation and new bone formation by cells held in vivo within subcutaneous diffusion chambers using a mouse SCID model. In this way, comparisons can be made with in vitro experiments. Targeting of cells to specific tissues in vivo may also be advised.

EXAMPLE 4

Demonstration of In Vivo Bone Formation

Human-derived osteoprogenitors from mesenchymal stem cells may be used. In vivo bone formation may be assessed using the subcutaneous implant model in severely compromised immunodeficient (SCID) mice and the diffusion chamber model. This provides a rapid and robust model to validate, in vivo, the efficacy for targeting of magnetic micro- and nanoparticles and provides a clear demonstration of bone formation. The diffusion chamber assay provides unequivocal demonstration of bone formation by implanted cells as opposed to host cells. The subcutaneous implant model remains the industry standard for the assessment of skeletal tissue formation and one of us (RO) has published on the use of both the sc and DC models under a project license to RO (30/1759) for assessment of skeletal tissue engineering[22]. In brief, selected human osteoprogenitor cells will be implanted subcutaneously in SCID mice for four weeks while for diffusion chamber studies, cells and magnetic particle composites will be placed into each diffusion chamber and the chambers implanted intraperitoneally into athymic nude mice (MFI-nu-nu; 4-6 weeks old; Harlan UK Ltd) for 10 weeks. Thereafter, diffusion chambers will be removed, fixed overnight (95% ethanol, 4° C.) and embedded=decalcified in poly(hydroxymethylmethacrylate) resin at 4° C. New bone formation will be assessed by histological techniques including frozen, paraffin and methylmethacrylate plastic sections. Assessment of cartilage and bone formed will be by histological examination using toluidine blue Giemsa, alcian blue/sirius red and Safranin-O staining. The model is currently run in Southampton under a project licence to RO (30/1759).

EXAMPLE 5

Targeting of Cells to Specific Sites in Vivo

This work will focus on delivery of magnetic particle-loaded cells to specific tissue sites via intra-arterial and intravenous injection. In brief, selected and expanded mesenchymal stem cells will be loaded with magnetic particles and injected by tail vein into anesthesized MF1nu/nu mice. The cells will be localised to a specific target site using external high-gradient NdFeB magnets. Control mice also will be injected, however, no magnet will be used for targeting. Targeting efficiency will be assayed using MRI (magnetic nanoparticles are used as contrast enhancement agents in clinical MR imaging) and SQUID magnetometry analysis of dissected, freeze-dried target tissue after 4, 7 and 14 days.

EXAMPLE 6

Preliminary experiments using the technique described herein have been conducted on human bone-derived mesechymal stem cells [Cambrex poietics-hMSC]. Cells cultured in alpha MEM with 10% FCS and 1% antibiotics, ascorbic acid (50 micrograms/ml) and beta-glycerophosphate (10 mM) (sample groups E-H) for 5 days.

Magnetic microparticles (d-4 μm) were coated with a biotinylated $\alpha_2/\delta$-1 subunit of a voltage gated calcium ion channel receptor antibody. After 4 days, particles were attached to the stem cells for 40 minutes via the calcium channel receptor. After 40 minutes, the cells were exposed to a 1 Hz magnetic field which applied a force of approximately 30 picoNewtons per particle (~2 particles/cell). After 2 hours 40 minutes, the particles were detached from the cells and removed by aspiration. The original culture media was returned to the samples which were then further cultured for another 24 hour period. RNA from the control and stimulated groups was collected at day five. Gene microarray analysis was performed on each of the samples. 8000 genes/sample were analysed using HG-Focus human genome chips (Affymetrix UK Ltd) in response to magnetic activation (upregulation and downregulation taken as two fold increase/decrease).

Microarray data from these experiments showed that the mechanical stimulation resulted in the downregulation of certain genes such as nerve growth factor and fibroblast growth factor (Table 1). This is an indication that the application of mechanical force using magnetic particles is guiding the stem cell differentiation away from the neuronal and fibroblast pathways. The upregulation of genes such as tetranectin in response to the mechanical force application indicates a differentiation of the cells towards an osteogenic pathway. Upregulation of genes involved in cytoskeletal reorganisation and cell adhesion proteins correlate with expected cell processes after force application.

TABLE 1

Results of microarray analysis showing the activity of specific genes related to differentiation and mechanical stimulation and their relative up- and downregulation compared to the non-stimulated control cultures.

| | |
|---|---|
| Total no. of genes expressed | 82 (42 ▲ 40 ▼) |
| Selection of genes expressed | Insulin-like GF binding protein 1 (2.1 fold ▲) |
| | FK506 binding protein (2.1 fold ▲) |
| | Zyxin (2.1 fold ▲) |
| | Integrin α5 (2 fold ▲) |
| | Early growth response 1 (2 fold ▲) |
| | Collagen typeIV alpha 3 (2.1 fold ▼) |
| | Nerve GF (2 fold ▼) |
| | Fibroblast GF 7 and 9 (2.1 and 2.5 fold ▼) |
| | Tetranectin (2.1 fold ▲) |

Symbols: ▲ upregulation and ▼ = downregulation.

The invention claimed is:

1. An in vitro method for the differentiation of an adult stem cell, the method comprising the steps of:
   (i) contacting, in vitro, an adult stem cell with a magnetizable particle so as to associate the adult stem cell and the magnetizable particle; and
   (ii) magnetically manipulating the associated adult stem cell and magnetizable particle by applying a magnetic field so that the adult stem cell differentiates.

2. The method of claim 1, wherein the adult stem is a mesenchymal stem cell or a bone marrow stromal cell.

3. The method of claim 1, wherein the method is for the differentiation of a. mesenchymal stem cell or a bone marrow stromal cell into connective tissue.

4. The method of claim 3, wherein the connective tissue is bone tissue, cartilage tissue, ligament or tendon.

5. The method of claim 1, wherein the magnetizable particle is tagged with at least one antibody or protein binding motif that recognizes an element of the adult stem cell.

6. The method of claim 1, wherein the magnetizable particle is tagged with at least one integrin, cadherin, selectin, immunoglobulin or RGD molecule.

7. The method of claim 1, wherein the adult stem cell expressed a mechano-activated transmembrane ion channel and the magnetizable particle is tagged with at least one antibody that recognizes the ion channel.

8. The method of claim 7, wherein the transmembrane ion channel is a potassium ion channel.

9. The method of claim 7, wherein the transmembrane ion channel is a TREK potassium ion channel.

10. The method of claim 7, wherein the transmembrane ion channel is the TREK-1 ion Channel.

11. The method of claim 1, wherein the magnetizable particle is magnetic or reacts in a magnetic field.

12. The method of claim 1, wherein the magnetizable particle comprises elemental iron (Fe) or a compound thereof, or a chromium compound.

13. The method of claim 1, wherein the magnetizable particle comprises an iron salt selected from the group consisting of: magnetite ($Fe_3O_4$), maghemite ($\gamma Fe_2O_3$), greigite ($Fe_3S_4$) and combinations thereof.

14. The method of claim 1, wherein the magnetizable particle has a size of from 1 nm to 10 μm.

15. The method of claim 1 comprising contacting a plurality of adult stem cells with a plurality of magnetizable particles and wherein the magnetizable particles have a mean size of 5000 nm or less.

16. The method of claim 1, wherein the applied magnetic field is a variable magnetic field.

17. The method of claim 1, wherein the applied magnetic field is a variable magnetic field which has a frequency of from 0.1 to 10 Hz.

18. The method of claim 1, wherein the magnetic field has a flux density of from 10 mT to 1400 mT.

* * * * *